US004001640B2

United States Statutory Invention Registration [19]

[11] Reg. Number: H1640

[45] Published: Mar. 4, 1997

Litchholt et al.

[54] REINFORCED LANDING SURFACE FOR MECHANICAL FASTENERS ON DISPOSABLE PRODUCTS

[75] Inventors: John J. Litchholt, Harrison; Dennis A. Thomas, Cincinnati; Keith W. Hammond, Hamilton, all of Ohio

[73] Assignee: The Procter & Gamble Company, Cincinnati, Ohio

[21] Appl. No.: 391,482

[22] Filed: Feb. 21, 1995

Related U.S. Application Data

[63] Continuation of Ser. No. 120,714, Sep. 13, 1993, abandoned.

[51] Int. Cl.[6] ..... A61F 13/15

[52] U.S. Cl. ..... 604/389

[58] Field of Search ..... 604/365–366, 604/377–391, 393–396; 602/75–79; 128/DIG. 15, DIG. 6; 24/306, 442–452

[56] References Cited

U.S. PATENT DOCUMENTS

| | | | |
|---|---|---|---|
| 2,625,161 | 1/1953 | Johnson | 604/366 |
| 3,085,309 | 4/1963 | Olson | 604/378 |
| 3,255,749 | 6/1966 | Smithers | 602/77 |
| 3,678,933 | 7/1972 | Moore et al. | 604/366 |
| 3,683,921 | 8/1972 | Brooks et al. | 604/366 |
| 3,768,479 | 10/1973 | Widlund | 604/366 |
| 3,863,304 | 2/1975 | Brumlik | 24/445 |
| 3,867,935 | 2/1975 | Eisdorfer et al. | 604/366 |
| 3,867,940 | 2/1975 | Mesek et al. | 604/377 |
| 3,971,381 | 7/1976 | Gibson | 604/366 |
| 4,067,609 | 1/1978 | Ness | 24/442 |
| 4,402,690 | 9/1983 | Redfern | 604/391 |
| 4,573,991 | 3/1986 | Pieniak et al. | 604/366 |
| 4,596,568 | 6/1986 | Flug | 604/378 |
| 4,695,500 | 9/1987 | Dyer et al. | 604/577 |
| 4,699,622 | 10/1987 | Toussant et al. | 604/389 |
| 4,834,738 | 5/1989 | Kielpikowski | 604/385.2 |
| 4,936,840 | 6/1990 | Proxmire | 604/391 |
| 5,176,670 | 1/1993 | Roessler et al. . | |
| 5,176,671 | 1/1993 | Roessler et al. . | |

FOREIGN PATENT DOCUMENTS

| | | | |
|---|---|---|---|
| 1140576 | 1/1969 | United Kingdom | 24/442 |

*Primary Examiner*—Charles T. Jordan
*Assistant Examiner*—Meena Chelliah
*Attorney, Agent, or Firm*—Harness, Dickey & Pierce, P.L.C.

[57] ABSTRACT

The present invention is directed to a mechanical fastening system for use with disposable absorbent products. More particularly, a reinforced landing surface is disclosed for securing a hook-type mechanical fastener thereto. The reinforced landing surface includes a fibrous non-woven layer and a scrim-like web that is attached in a composite arrangement to the fibrous non-woven layer. The mechanical fasteners include a plurality of hooks, such as those used in a hook and loop type fastener which extend through the scrim-like web and penetrate the non-woven fibrous layer and become intertwined therewith. Depending upon the fastening requirements, the pattern of the scrim-like web may be repetitive, variable, continuous or discrete.

1 Claim, 2 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

REINFORCED LANDING SURFACE FOR MECHANICAL FASTENERS ON DISPOSABLE PRODUCTS

This is a continuation of U.S. patent application Ser. No. 08/120,714, filed Sep. 13, 1993, now abandoned.

BACKGROUND OF THE INVENTION

I. Field of the Invention

The present invention relates generally to disposable absorbent articles and, in particular, to an improved mechanical fastening system for securing placement of the article on the body of the user.

II. Background Art

Infants and other incontinent individuals wear disposable absorbent articles, such as diapers, to receive and contain urine and other body exudates. In order to secure placement of the absorbent article, various fastening systems have been employed for fastening the waistband portions of the disposable article around the waist of the wearer. Most conventional fastening systems include fastener tabs that are attached to the rear waistband portion of the disposable article. As the disposable article is placed on the user's body, the rear waistband portion is caused to overlap the front waistband portion such that the fastener tabs can be releasably secured thereto.

As is known, a majority of commercially-available disposable absorbent articles, such as diapers and incontinent briefs, employ an adhesive fastening system in which adhesive tabs on the rear waistband portion are stuck onto the front waistband portion, thereby closing the diaper. During normal use, however, it is common for the adhesive tabs to be repeatedly reopened and subsequently reclosed to check the soiled condition of the diaper. Thus, failure of the diaper may result if the adhesive bond is weakened due to contamination. Unfortunately, the likelihood of contamination occurring as a result of using substances (i.e., talc powder, baby oil, ointments and the like) to assist in making the wearer more comfortable is fairly common. Yet another problem associated with adhesive fastening systems is that a misapplication of the adhesive tab onto the backing surface of the diaper's front waistband portion may cause a tear in the backing surface, with a portion of the backing surface remaining attached to the adhesive tab, thereby precluding reattachment of the adhesive tab to the diaper.

As an alternative to adhesive fastening systems, it is becoming increasingly more common to employ a mechanical fastening system in disposable articles. For example, hook and loop fastening systems, utilizing fasteners such as Velcro®, wherein the hook material is molded of a copolymer and the loop material is a fabric of polyester fiber having a napped surface are currently being utilized in the industry. However, one problem inherent with such hook and loop fastening systems is their limited resistance to peel and/or shear forces which naturally result due to differential movements of the wearer. Yet another problem commonly associated with hook and loop fastening systems is that a portion of the loop material fabric tends to tear away each time the tab of hook material is peeled away.

While the above-mentioned hook and loop mechanical fastening systems offer some advantages over the earlier known adhesive fasteners, they tend to still fall short of fulfilling the overall need for providing a highly-reliable fastening mechanism for disposable products. More particularly, such systems fail to address the need for maintaining secure placement of the disposable article in view of the anticipated differential movements (i.e., bending, twisting, etc.), re-adjustments and/or manipulations made by the individual wearing the product.

It is therefore an object of the present invention to provide an improved mechanical fastening system for disposable absorbent articles having a reinforced landing surface for releasably securing a mechanical fastener thereto.

It is an additional object of the present invention to provide a reinforced landing surface which will provide augmented securement of the mechanical fasteners upon differential movement, adjustment or manipulation by the individual wearing the product.

It is another object of the present invention to provide a reinforced landing surface which will limit, and preferably, eliminate tearing thereof upon peeling away the previously attached mechanical fastener.

Yet another object of the present invention is to provide a reinforced landing surface which is soft and resilient for improved tactile aesthetics, and yet provides a rigid anchoring site for releasably retaining a mechanical fastener.

These and other advantages of the present invention will be more readily apparent when considered in reference to the following description and when taken in conjunction with the accompanying drawings.

SUMMARY OF THE INVENTION

The present invention is directed to the incorporation of a reinforced landing surface into the fastening system of a disposable absorbent article for releasably retaining mechanical hook-type fasteners. More specifically, the reinforced landing surface is a composite pad which includes at least one layer of a non-woven fibrous material and at least one layer of a scrim-like web attached to the non-woven fibrous material. The apertures of the scrim-like web are patterned to provide an anchoring site (i.e., rigid surface) through which the hooks of the mechanical fastener extend for improving the fastening system's resistance to peel or shear.

According to one preferred embodiment, the scrim-like web is attached to the fibrous non-woven material such that a significant number of its fibrous strands extend through the apertures of the web. Upon connecting the mechanical hook-type fastener to the reinforced landing surface, the head portions of the hooks project through the apertures of the scrim-like web and becomes intertwined and entangled with the fibrous strands to retain the disposable product in a useful position. A variety of materials can be used to form the fibrous layer(s) such as nylon, polyester, bi-component fiber, polyethylene, polypropylene, rayon and wood pulp, among others. In addition, the pattern of the scrim-like web can be varied so long as the apertures are sufficiently large to receive the head portion of the hooks and yet small enough to provided adequate resistance against the removal of the hooks therefrom. The scrim-like web can be formed via a number of differing techniques including, but not limited to Gravure printing, hot melt screen printing, spiral glue type applicators, or through extrusion.

BRIEF DESCRIPTION OF THE DRAWINGS

While the specification concludes with claims particularly pointing out and distinctively claiming the subject matter which is regarded as forming the present invention, it is believed that the invention will be better understood from the following description, taken in conjunction with the accompanying drawings wherein like reference numerals are used for substantially identical elements, and in which:

DETAILED DESCRIPTION OF THE PREFERRED EMBODIMENT

Figure 1:
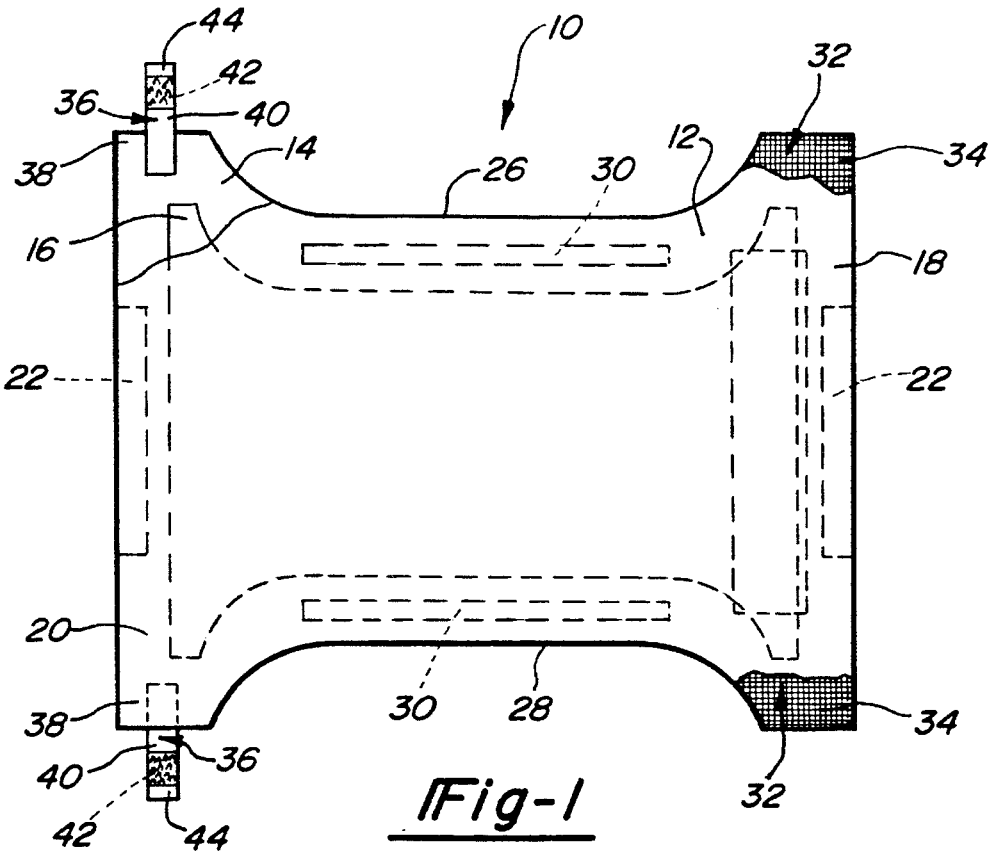
FIG. 1 is a top plan view of an exemplary disposable absorbent article incorporating an improved mechanical fastening system according to any of the various preferred embodiments of the present invention.

In general, the present invention is directed to an improved mechanical fastening system of the type used in disposable absorbent articles. More specifically, the present invention relates to the use of a reinforced landing surface on disposable absorbent articles for receiving and releasably retaining the hooks of the mechanical hook-type fastener. As used herein the term "disposable absorbent article" refers to products which absorb and contain body exudates and, more specifically, refers to products which are placed against or in proximity to the body of the wearer to absorb and contain the various exudates which are discharged from the body (e.g., urine, feces) and which products are intended to be discarded after a single use (i.e., they are not intended to the be laundered or otherwise restored or reused).

An exemplary embodiment of a disposable absorbent article is shown in the drawings as a disposable diaper which includes the improved mechanical fastening system of the present invention. In general, the improved fastening system of the present invention includes a mechanical hook-type fastener positioned at one of the longitudinal ends of the disposable diaper and a reinforced landing surface positioned at the other longitudinal end thereof. The longitudinal ends define waistband portions of the disposable diaper which are constructed to overlap when worn to encircle the waist of the user. Interengagement of the hooks of the mechanical fastener with the reinforced landing surface following overlapping alignment of the waistband portions is adapted to releasably secure the disposable diaper in a snug, yet comfortable, fit on the user. However, it is to be understood that the novel principles and features of the improved mechanical fastening system, to be hereinafter set forth with greater specificity, could likewise be incorporated into other suitable disposable articles and the like.

Figure 2:
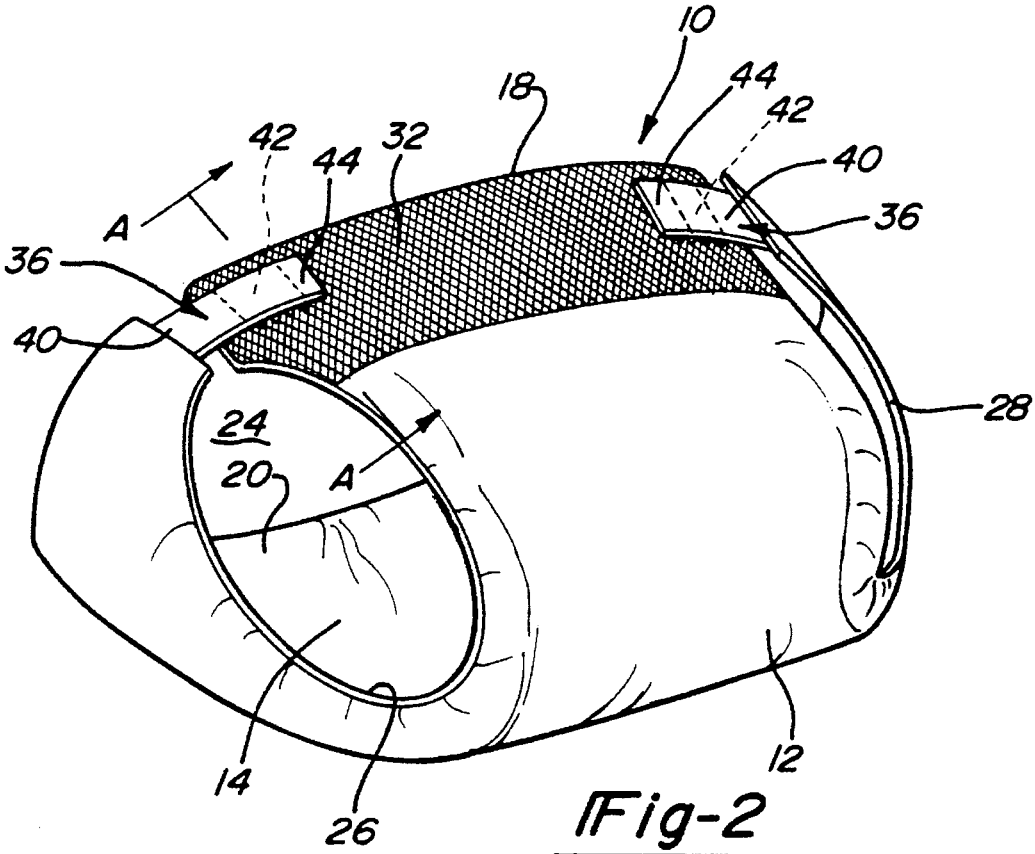
FIG. 2 is a perspective view of the disposable product of FIG. 1 illustrating the mechanical fastening system retaining the disposable product in a useful position.

With particular reference to FIGS. 1 and 2, a disposable absorbent article, hereinafter disposable diaper 10, is shown to basically include a liquid impermeable outer backing sheet 12, a liquid permeable inner top sheet 14 joined with backing sheet 12, and an absorbent body or core 16 positioned between the backing sheet 12 and the top sheet 14. The backing sheet 12 may be made from any one of a number of different liquid impermeable materials, including but not limited to, polyethylene and polypropylene films. The absorbent core 16 may include a variety of materials which are generally compressible, conformable, and non-irritating to the wearer's skin yet capable of absorbing and containing liquids and certain body exudates, such as urine and feces. Examples of suitable materials useful for forming the absorbent core 16 include air-laid, cellulosic fibers such as wood pulp fluff, a mixture of cellulose fibers and synthetic material polymer fibers, such as an air-laid blend of cellulosic fibers and melt blown polyolefin fibers, absorbent foams, absorbent sponges, absorbent hydro-gel materials, and super absorbent polymers among others. In addition, the absorbent care 16 may also be treated with an effective amount of an inorganic or organic high absorbency material to enhance the absorptive capabilities of the product. Suitable inorganic materials include absorbent clays and silica gels among others. Organic high absorbency materials include, as examples, pectin, gums, and certain synthetic materials such as synthetic hydro-gel polymers including, but not limited to, carboxyl methyl cellulose, alkali metal salts of polyacrylic acids, polyacrylamides, polyvinyl alcohols, and polymers and co-polymers of vinyl sulfonic acid. If the absorbent core 16 is comprised of more than one constituent pan or material, one part or material of the absorbent body portion may not be absorbent or liquid permeable, so long as the combination of parts or materials has some degree of absorbency including to a certain degree the properties set forth above.

The top sheet 14 is generally compliant, soft feeling and nonirritating to the wearer's skin. Further, the top sheet 14 is liquid permeable, thus permitting liquids to readily penetrate through its thickness. Suitable top sheets 14 may be manufactured from a wide range of materials such as foamed thermoplastic films, apertured plastic films, porous foams, reticulated formed, natural fibers (e.g., wood or cotton fibers), synthetic fibers (e.g. polyester or polypropylene fibers) or from a combination of natural and synthetic fibers and from formed films. While not of particular importance to the present invention, the top sheet 14 and back sheet 12 are fastened together peripherally by a suitable adhesive or heat bonding process.

With continued reference to FIGS. 1 and 2, the disposable diaper 10 is also shown to include front and rear waistband portions 18 and 20. In addition, the waistband portions 18 and 20 are shown schematically to include an elastic member 22, such as an elastomeric stretch bonded laminate, to provide the disposable diaper 10 with improved form-firing capabilities. Elastic members 22 are adapted to gather waistband portions 18 and 20 to provide a snug dynamic seal about the waist of the wearer. Disposable diaper 10 also includes a pair of leg openings 24 that are formed along the lateral side margins 26 and 28 of diaper 10 and which are also shown to include an elongated elastic member 30 that is implanted adjacent each lateral side margin. Typically, the elastic member 30 used for the lateral side margins of the diaper 10 are formed from synthetic and natural rubbers and are adapted to gather the side margins for providing an elastic dynamic seal about the legs of the wearer. As best seen from FIG. 1, the central portion of the disposable diaper 10 is narrower than the waistband portions 18 and 20 such that the disposable product has, in plan view, an overall hourglass shape. It will be understood that the above-described structure and construction of diaper 10 is merely exemplary of but one disposable absorbent article to which the novel principles of the present invention, to be described hereinafter with greater specificity, can be readily applied.

In general, the present invention is directed to the incorporation of an improved mechanical fastening system into disposable diaper 10. More particularly, the mechanical fastening system of the present invention is directed to utilization of a reinforced composite landing surface 32 that is particularly well adapted for engagement with hook-type mechanical fasteners to secure placement of disposable diaper 10 on the wearer. To this end, a reinforced landing surface 32 is provided on backing sheet 12 in close proximity to each lateral edge or corner section 34 of front waistband portion 18. Preferably, the reinforced landing surface 32 extends completely across the lateral edge as shown in FIG. 2 to allow for adjustability of the diaper. Similarly, a hook-type mechanical fastener tab 36 is provided at each corner section 38 of rear waistband portion 20. In use, the fastener tabs 36 are engageable with the reinforced landing surfaces 32 for fastening the front and rear waistband portions 18 and 20 together in a partially overlapping relationship about the waist of the wearer.

Each fastener tab 36 includes an elongated tape or web 40 and a hooked segment 42 secured thereto. Hooked segment 42 includes a plurality of hooks 46 for engaging its respective one of the reinforced landing surfaces 32. Preferably, web 40 is manufactured of a durable material, such as a polypropylene film, suitable for hosting the hooked segment 42. The fastener tabs 36 may be adhesively fastened to backing sheet 12 or, in the alternative, adhesively fastened between top sheet 14 and backing sheet 12. Preferably however, the fastener tabs 36 will be of a Y-shaped tape tab construction as disclosed in U.S. Pat. No. 3,848,594 which issued Nov. 19, 1974 to Buell, which is hereby incorporated by reference. The Y-shaped tape tab essentially includes first and second portions which are adhered or otherwise attached to backing sheet 12 and top sheet 14, respectively, and an extending portion which hosts the hooked segment. Under the Y-shaped tape tab embodiment any forces imposed on the fastening tab are transmitted to both the backing sheet and top sheet. As a further alternative, web 40 for each fastener tab 36 may be formed as an integral extension of backing sheet 12. The hooked segment 42 is typically bonded to the web 40 using either a suitable adhesive or by a heat bonding process to face upwardly in the direction of top sheet 14. A finger tab 44 is exposed at the distal end of each web 40 for ease in grasping the fastener tabs 36 to release them following initial fixation to landing surfaces 32.

In general, the hooks 46 on hooked segments 42 may be similar to those used with otherwise conventional hook and loop fastening systems. Typically, the hooks 46 are produced from a suitable polymeric material such as a polypropylene co-polymer. In addition, the hooks 46 are tapered from a base portion 48 to a top portion 50 which terminates with a generally spherical head portion or tip 52. A preferred hook design as shown in FIGS. 3 through 6 is demonstrated in detail in U.S. Pat. No. 5,058,247 which issued on Oct. 22, 1991 to Thomas et al., which is hereby incorporated by reference. According to the Thomas et al. patent the heads 52 of the hook are substantially without sharp edges for inhibiting potential abrasion of the structure which could possibly lead to fabric tears. Further, and more importantly, the Thomas type hook is less likely to irritate the wearer's skin than other known fastening hook designs.

It should be noted that the hooks 46 may be arranged in an alternating arrangement wherein immediately adjacent rows of hooks 46 have their inner arcuate portions 54 facing in opposite directions. Such an arrangement provides multi-direction retention of hooks 46 within and on reinforced landing surfaces 32. Moreover, the hooks 46 are substantially rigid when free standing but are flexible enough to engage the reinforced landing surfaces 32. Alternatively, the hooks 46 can be arranged uni-directionally thus providing increased fastening retention along a single direction. As will be appreciated from the following discussion, the overall height, thickness, spacing density and the like of the hooks 46 is a direct function of the characteristics of the particular composition defining reinforced landing surfaces 32.

Each of the embodiments to be hereinafter described for reinforced landing surfaces 32, and which are shown in more detail with reference to FIGS. 3 through 6, generally include at least one layer of a scrimlike web 56 and at least one layer of non-woven fibrous material 58 that are compositely attached to the backing sheet 12. In addition, the reinforced landing surfaces 32 typically are devoid of both absorbent material and an absorbent top sheet. As best seen from FIG. 2, each landing surface 32 is oriented to extend outwardly from backing sheet 12 for inter-engagement with hooks 46 of fastener tabs 36.

As demonstrated in FIGS. 3 through 6, the reinforced landing surfaces 32 are typically provided on backing sheet 12 at the front corner sections 34 of the disposable diaper 10. While shown as two distinct landing areas, it is contemplated that plural strips or one continuous strip of the reinforced composite defining landing surfaces 32 can also be used. Preferably, the layer of scrim-like web 56 is made of a material such as ethyl vinyl acetate (EVA), olefins, block co-polymers, various other polymers, silicas, waxes and other suitable materials. The scrim-like web 56 is typically patterned such that its apertures 60 have a substantially square or rectangular shape. Again, the size of each aperture 60 is directly correlative to the size of the hooks 46 formed on hook segment 42 of fastener tabs 36. However, scrim-like web 56 is patterned to provide a rigid "anchoring" surface for retaining portions of hooks 46 extending through aperture 60 against undesirable shear and/or peel. The scrim-like web 56 can be formed by a variety of processes including, but not limited to, Gravure printing, hot melt screen printing, spiral glue type applicators, or through extrusion. As noted, the pattern of the scrim-like web 56, whether continuous or intermittent, is designed to provide a rigid anchoring substrate for receiving the hooks 46 of fastener tabs 36.

The layer of non-woven fibrous material 58 includes a multiplicity of fibrous strands 62 and is preferably arranged such that some of the strands 62 extend partially into and through the apertures 60 of the scrim-like web 56. The fibrous layer 58 may be made of a variety of materials including, but not limited to, nylons, polyesters, bi-component fibers, polyethylene, polypropylene, rayon and wood pulp, among others. As noted, the reinforced landing surface 32 is a composite structure formed by extruding, screen printing, adhesively attaching or otherwise combining the scrim-like web 56 with the layer of nonwoven fibrous material 58.

As shown most clearly with reference to FIGS. 3 through 6, the composite reinforced landing surface 32 can be varied in structure to accommodate the specific fastening requirements of a particular disposable absorbent product. In addition to improved peel and shear resistance, reinforced landing surface 32 is relatively soft and resilient to promote enhanced tactile aesthetics. Since the structures, while varied, utilize like components arranged differently to carry out the intended purposes of the invention, like reference numerals will be used to describe like components in FIGS. 3 through 6.

Figure 3:
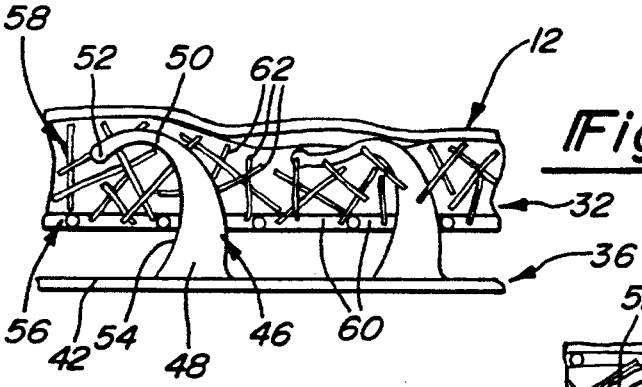
FIG. 3 is a side view taken generally along line A—A of FIG. 2 illustrating a first embodiment of a reinforced landing surface that is associated with the mechanical fastening system of the present invention.
Figure 4:
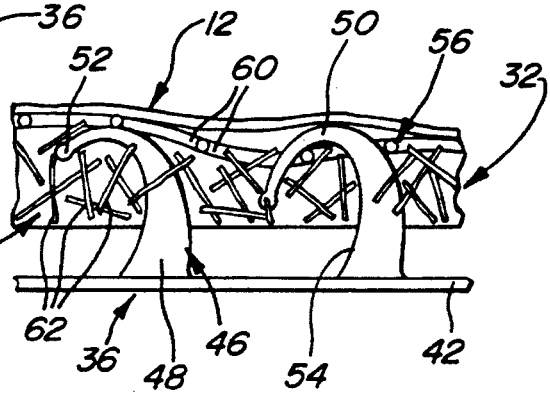
FIG. 4 is a side view of an alternative embodiment for the reinforced landing surface of the present invention.

With particular reference now to FIG. 3, the layer of non-woven fibrous material 58 is shown attached and located adjacent to the backing sheet 12 with the scrim-like web 56 being positioned over the fibrous material 58 and spaced apart from the backing sheet 12. Upon engagement of the mechanical hook-type fastener tabs 36 with the landing surfaces 32, the hooks 46 penetrate the apertures 60 of scrim-like web 56 such that the heads 52 of hooks 46 become intertwined and entangled with the fibrous strands 62 of the fibrous material 58. As shown in FIG. 4, the scrim-like web 56 can alternately be positioned substantially adjacent to the backing sheet 12 with the layer of fibrous material 58 positioned over the scrim-like web 56. Again, the head portions 52 of the hooks 46 randomly extend through the apertures 60 formed in the scrim-like web 56, thus becoming entangled with the fibrous strands 62 of the non-woven fibrous material 58. As shown in FIG. 4, the hook 46 illustrated on the right extends through the scrim-like web 56 while the hook 46 on the left does not.

Figure 5:
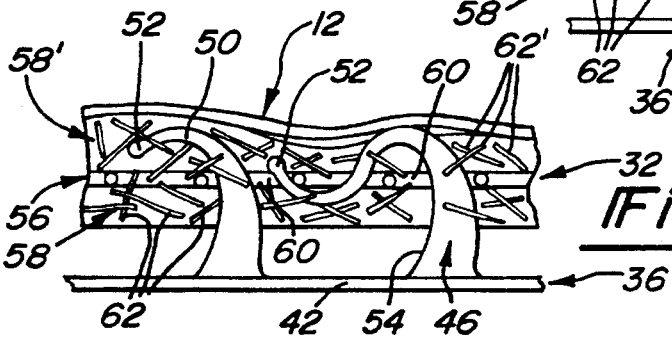
FIG. 5 is a side view of another alternative embodiment for the reinforcement landing surface of the present invention.

FIG. 5 demonstrates another embodiment for landing surface 32 wherein the scrim-like web 56 is embedded between first and second layers of the fibrous non-woven material 58 and 58', respectively, such that the heads 52 of the hooks 46 extend through the fibrous strands 62 in the first layer of fibrous material 58, randomly through the apertures 60 in scrim-like web 56 and then through the fibrous strands 62' in the second layer of fibrous material 58', thereby becoming intertwined. As shown in FIG. 5, the hook 46 on the right passes through the scrim-like web 56 three times while the hook on the left only passes through once.

Figure 6:
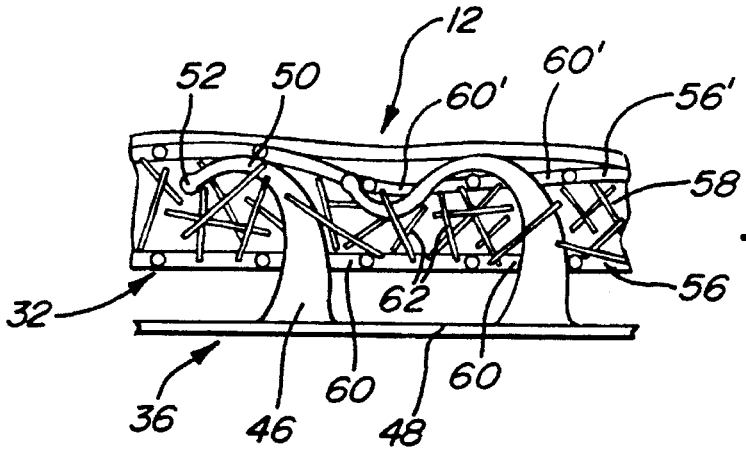
FIG. 6 is a side view of yet another alternative embodiment of the reinforcement landing surface of the present invention.

According to the embodiment of FIG. 6, the layer of fibrous material 58 is sandwiched between first and second scrim-like web layers 56 and 56' with one of the scrim-like layers 56' being substantially adjacent to the backing sheet 12. Upon contacting the reinforced landing surface 32, the head portions 52 of the hooks 46 project through the apertures 60 in the first scrimlike web 56, become intertwined with the fibrous strands 62 of fibrous material 58, and further extend randomly through the apertures 60' formed in the second scrimlike web 56'. As shown in FIG. 6, the hook 46 on the right passes through second scrim-like web 56' at two locations while the hook 46 on the left does not pass through second scrim-like web 56'. It should be noted by those skilled in the art that the reinforced landing surface 32 according to the teachings of the present invention may take on a variety of embodiments as long as the underlining concept of utilizing a composite formed of at least one scrim-like web portion 56 and a non-woven fibrous material 58 is utilized.

Turning again specifically to FIGS. 1 and 2, the means for securing the hook-type fastener tabs 36 to the reinforced landing surfaces 32 will be demonstrated in greater detail. The fastener tabs 36, which are generally attached to the rear corner sections 38 to extend laterally at least about 1.5 inches past the edge thereof, are positioned proximate to the landing surfaces 32 thus providing the leg holes 24 through which the wearers legs extend. The fastener tabs 36 are then brought into contact with the reinforced landing surfaces 30 such that hooks 46 project into and through the composite landing surface 32 as previously described with reference to FIGS. 3 through 6. Upon attachment, the feature of entangling the head 52 of the hooks 46 with the fibrous strands 62 of the layers of fibrous material 58 is further enhanced by normal differential movement of the wearer. As the wearer moves, hooks 46 move within the reinforced landing surface 32 and become increasingly entangled within the reinforced landing surface 32 structure. Thus, as the wearer shifts about within the disposable product, the disposable product becomes increasingly resistant to undesired peel and shear forces.

While the reinforced landing surface 32 of the present invention has been described as being positioned at the front corners 34 of the disposable products, it should be understood by those skilled in the art that the reinforced landing surface 32 could be positioned at various other locations on the disposable product. For example, the reinforced landing surfaces 32 could be positioned along the entire front waistband portion 18 thus providing an added adjustability feature. Further, it should also be understood that the mechanical fastener tabs 36 could also be provided at various positions.

While particular embodiments of the present invention have been illustrated and described, it would be obvious to those skilled in the art that various other changes and modifications can be made without departing from the spirit and scope of the invention. It is, therefore, intended to cover in the appended claims all such changes and modifications that are within the scope of this invention.

What is claimed is:

1. A composite reinforced landing surface for receiving the hooks of a hook-type fastener, said composite reinforced landing surface comprising:

a layer of a scrim-like web material having a plurality of apertures; and a layer of a non-woven fibrous material having a plurality of fibrous strands;

whereby upon connecting the fastener to said reinforced landing surface, the hooks extend at least partially through said apertures and become intertwined and entangled with said fibrous strands.

* * * * *